United States Patent
Ko et al.

(10) Patent No.: US 6,569,386 B1
(45) Date of Patent: May 27, 2003

(54) PROCESS FOR PROVIDING A TITANIUM DIOXIDE LAYER ON A MATERIAL THAT CONTAINS A LIGHT ABSORBING SUBSTANCE AND THE PRODUCT SO FORMED

(76) Inventors: Jong Ho Ko, 3207 Henderson Mill Rd., Apt. P8, Atlanta, GA (US) 30341; Samuel Ko, 3207 Henderson Mill Rd., Apt. P8, Atlanta, GA (US) 30341

(*) Notice: Subject to any disclaimer, the term of this patent is extended or adjusted under 35 U.S.C. 154(b) by 0 days.

(21) Appl. No.: 09/679,967

(22) Filed: Oct. 5, 2000

(51) Int. Cl.[7] .............................. A62B 7/08; B01J 19/08; A61L 9/00; B05B 5/025; B05B 5/00
(52) U.S. Cl. .................. 422/120; 422/123; 422/186; 422/306; 118/620; 427/157; 427/158; 427/332; 427/333
(58) Field of Search ................ 422/1, 5, 24, 28–29, 422/292, 120–121, 123, 186; 118/620; 427/157–158, 332–333

(56) References Cited

U.S. PATENT DOCUMENTS 3,994,851 A  * 11/1976 Chang ................... 260/29.4 R
5,690,922 A  * 11/1997 Mouri et al. ............... 424/76.1

* cited by examiner

Primary Examiner—Robert J. Warden, Sr.
Assistant Examiner—Monzer R. Chorbaji
(74) Attorney, Agent, or Firm—Smith, Gambrell & Russell, LLP

(57) ABSTRACT

A metallic compound layer exhibiting a photocatalytic activity function is formed on the surface of light absorbing material so as to provide the property of deodorizing air or an object coming in contact with the material. Preferably, the metallic compound layer is fixed on the surface of the light absorbing material. Alternatively, the metallic compound layer is formed as a material in which the surface region includes an outer portion mainly formed of a metallic mixture including a metallic oxide, such as titanium oxide. As a method of manufacturing the light absorbing material is coated with a metallic compound for improving photocatalytic activity, and then is processed into a desired shape.

10 Claims, 1 Drawing Sheet

PROCESS FOR PROVIDING A TITANIUM DIOXIDE LAYER ON A MATERIAL THAT CONTAINS A LIGHT ABSORBING SUBSTANCE AND THE PRODUCT SO FORMED

FIELD OF THE INVENTION

The present invention relates to a process for forming a luminous layer that absorbs and emits light, on a metallic or non-metallic plate having a surface coated with a photo-catalytic titanium dioxide layer. The plate having the luminous material layer provides photo-catalytic activity and is formed with a metallic compound layer. This plate exhibits the characteristics of deodorization, antibiotic activity, and prevention of ambient contamination.

BACKGROUND OF THE INVENTION

This invention relates to a surface treatment process for forming a base metal or non-metal having a light absorbing material present and metallic compound layer having photocatalytic activity.

Methods of deodorization are known in which an apparatus or a piece of equipment is used for exhausting or masking odors. The removal of molds by means of chemicals is generally performed by selecting an appropriate chemical according to the kind of mold.

Odors and molds are attributable to microorganisms, such as bacteria, yeasts and molds, and animal and plant cells. Accordingly, the attempt to deodorize and prevent molds and fouling can, in principle, be considered as the destruction of these cells, i.e., sterilization. Known methods of sterilization include heating, irradiation with ultraviolet or other radioactive rays, cell destruction by means of ultrasonic waves, electric sterilization, gas sterilization, and sterilization using chemicals including antibiotics. In addition, a sterilization method using fine particles of a photocatalyst is also known. Photocatalysts such as titanium dioxide are known to exhibit photocatalytic function by means of a light of a specific wavelength and possess deodorizing and antimold functions through their oxidizing action.

Conventionally, titanium dioxide, iron oxide, tungsten oxide, silicon oxide and the like, or such metals optionally with second metal, such as platinum, thereon for the purpose of improving the catalytic function are used as photocatalysts. To make use of the deodorizing and antimold functions, such metals are normally pulverized into fine particles to form a fixed film on a surface, or the fine particles are used by being dispersed in an object to be treated.

Various studies have been made regarding methods of imparting deodorizing and antimold functions to materials by making use of the photocatalytic function, however particles are troublesome to handle as materials. Known fixed films have only been used experimentally, and their strength is not sufficient, and the fabrication of photocatalytic materials into thin films has been industrially difficult, and has not yet been put into commercial use.

It is an object of the present invention to provide a material having a titanium dioxide layer exhibiting the characteristic of photocatalytic activity in addition to a light absorbing material, which provides the base light for photocatalytic activity of titanium dioxide.

A further object of the present invention is to provide a material which exhibits the characteristics of deodorization, antibiotic activity and prevention of ambient contamination in darkness after a short exposure to light irradiation.

It is also an object of this invention to provide a metal surface with a titanium dioxide coating having photocatalytic activity which can be used in applications where the base metal is useful, including construction materials, filtration systems, food processing equipment and containers, garbage or trash containers, and the like.

SUMMARY OF THE INVENTION

This invention provides a material (metallic or non-metallic) having a surface coated with a metallic compound which exhibits photocatalytic activity in addition to the presence of a light absorbing material. The materials to be coated with the metallic compound advantageously are metals, plastics, composites, paper and the like. Advantageously the metallic compound layer is formed of anatase $TiO_2$.

The photocatalytic activity of the present inventive coated material is useful in any application in which the base material is useful, including in construction materials, filtration systems, food processing equipment and containers, garbage or trash containers, and the like.

DETAILED DESCRIPTION OF PRESENT INVENTION

Figure 1:
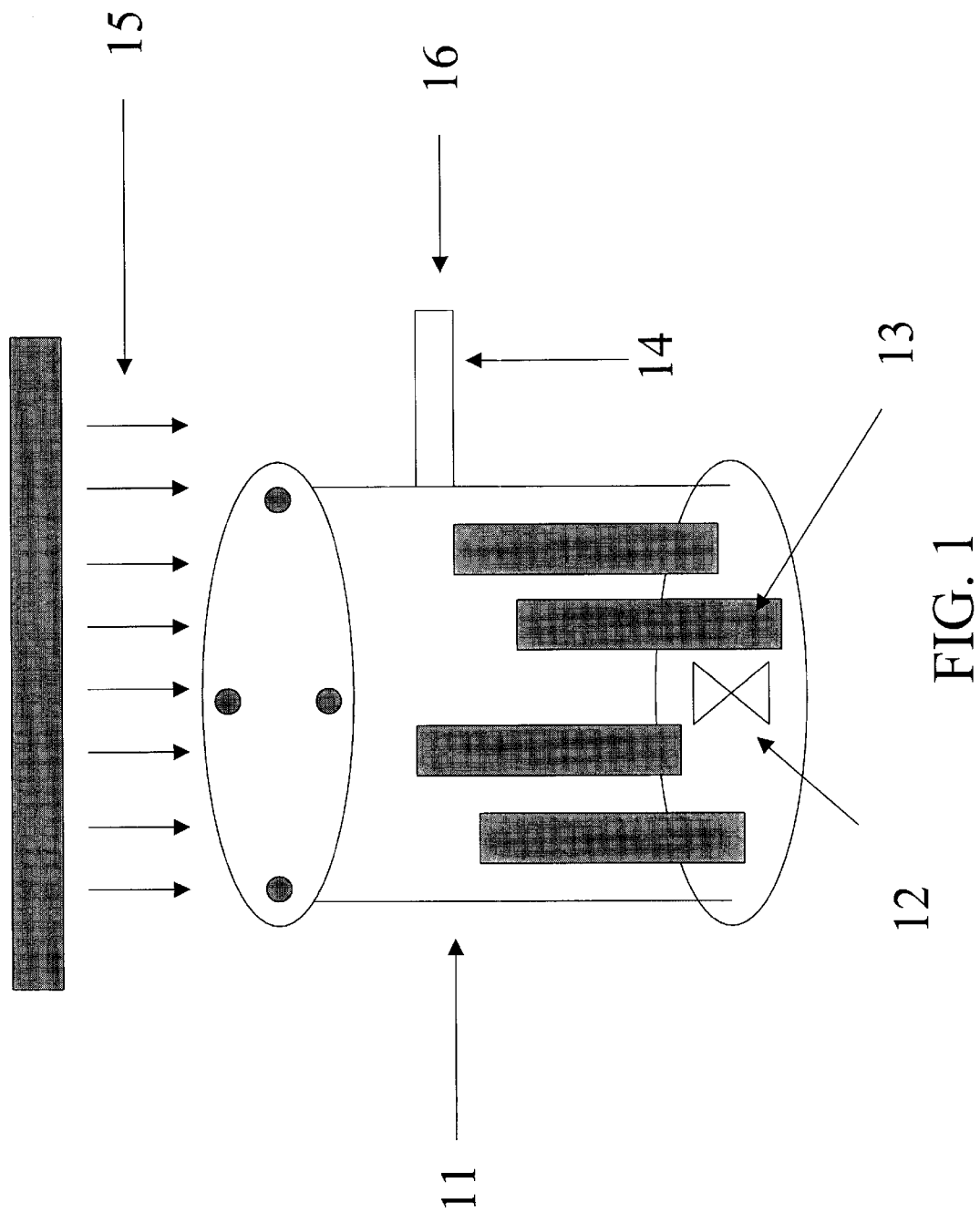
FIG. 1 depicts the testing apparatus used to test the efficacy of the products of the present invention.

The present invention is unique because the photocatalytic activity can be performed in a place where the material has exposure to a limited amount of light. Since the luminous material absorbs and stores light and emits light in the dark, the photocatalytic activity continues to be very active in the dark while the luminous material emits light. Titanium dioxide can perform limited deodorization, antibiotic activity, and prevention of ambient contamination even under conditions without irradiation of light. Thus, the present luminous material can be used very effectively to enhance the photocatalytic in a place where the exposure to a light is limited, such as refrigerators, closets, indoor places, air and water filtration systems, food processing and storage, refuse containers, and the like.

The luminous material upon exposure to a light source, phosphorescents and will store light. In the dark the material appears to glow. The luminous materials used herein are a combination of flourescent color pigments combined with phosphorescent pigment.

Glow in the dark products work by converting absorbed light energy into visible light. The light energy that is emitted during excitation is called fluorescence while that which is given out in the dark is called phosphorescence. To lengthen the afterglow process, a photo storage material is used. For instance, the traditional photo storage material widely used in the watch industry is zinc sulfide with copper added. This product has low brilliance with a decay time of 20 minutes. It also turns black after prolonged exposure to UV rays or sunlight. To lengthen the afterglow of this product, some manufacturers have added a radioactive substance called promethium to it. This enables it to glow for a few hours but with harmful radioactive rays.

There are many types of luminous material that emit different colors-green, blue, violet, etc. However, it has been found that UV light irradiation is one of the most effective for the photocatalytic activity of titanium dioxide, although a light source from fluorescent lamp may be sufficient for an effective exhibition of the catalytic activities. For that reason, the preferred luminous materials used in the present invention are materials that emits a violet color (430 nm), which is very close to the ultraviolet light wavelength (UVA), 315–400 nm.

The human eye responds to light with wavelengths from about 790 nm (red) to 430 nm (violet). Light with wavelengths shorter than the human eye sees is called ultraviolet (beyond violet) light.

Ultraviolet (UV) light is contained in the range of wavelengths produced by the sun. Most UV light is absorbed by the ozone layer or reflected back into space so only a small amount reaches the surface of the Earth. Sunlight is received as direct rays and as diffuse light, i.e. skylight which has been scattered by the atmosphere. The sky is blue because air molecules scatter the shorter wavelength blue light more than the red light. UV light is scattered even more than blue light. If we could see in the UV, the sun would appear as a dull disk in a uniformly bright sky.

UV radiation is subdivided into three wavelength bands: UVA (315–400 nm), UVB (290–315 nm) and UVC (220–290 nm). UVA radiation is important in the generation of photochemical smog and also in fading and damage to plastics, paints and fabrics. UVC is totally absorbed by ozone and other gases, and does not reach the earth's surface. Only 1% of solar radiation is within the UVB band, and most of this is absorbed by ozone.

Referring to FIG. 1, which depicts the test apparatus used to verify the efficacy of the products of the present invention, closed container 11, advantageously transparent, has a circulation fan 12, a valve 14 to insert gas dector 16 and a source of UV light 15. Plates 13 having titanium dioxide and luminous material thereon are inserted in container 11 for testing.

The metallic compound used in the present invention is selected from the group of metallic compounds that are activated upon being irradiated with light. For example, it is possible to use at least one compound selected from the group consisting of titanium dioxide, iron oxide, silver oxide, copper oxide, aluminum oxide, tungsten oxide, silicon oxide, zinc oxide, and strontium titanate. Metals or other metal oxides modifying the metal oxide may be used to promote the photocatalytic reaction i.e. it is possible to use at least one compound selected from the group consisting of platinum, palladium, gold, silver, copper, nickel, rhodium, niobium, tin, cobalt, ruthenium oxide, and nickel oxide. As the amount added to modify the metal oxide, it is preferable to use such metals or metal oxides in the range of from 0.01 to 20 wt. % with respect to the metal oxide in the present invention.

Advantageously the following may be used instead of titanium dioxide: $ZnO$, $SrTiO_3$, $CdS$, $CdO$, $CaP$, $InP$, $In_2O_3$, $CaAs$, $BaTiO_3$, $K_2NbO_3$, $Fe_2O_3$, $Ta_2O_5$, $WO_3$, $SaO_2$, $Bi_2O_3$, $NiO$, $Cu_2O$, $SiC$, $SiO_2$, $MoS_2$, $MoS_3$, $InPb$, $RuO_2$, and $CeO_2$.

The metal oxide may be prepared by high-temperature sintering of a metal, electrolytic oxidation, a chemical deposition process, a vacuum deposition process, a coating process, a coprecipitation process, an evaporation oxidation process such as a metallic halogenation process, neutralization and hydrolysis of an inorganic metal salt, hydrolysis of a metal alkoxide, a sol-gel process, and the like. Alternatively, a commercially available product may be used. As the method of modifying the aforementioned metal or metal oxide, it is possible to use a conventional method such as impregnation, precipitation, ion-exchange, optoelectrodeposition, kneading, or the like.

In the present invention, the method of forming a thin film of a metal oxide on the material, preferably is a method in which a metal oxide is fixed on a part or the whole of a surface of material having a planar, curved or complicated surface by a method, selected from the group consisting of spray coating, dip coating, spin coating, sputtering, and the like.

Light energy based on irradiation includes a wavelength region corresponding to the excitation of photocatalysis. Specifically, it is preferable to use light energy which includes an ultraviolet wavelength below 400 nm, which contributes to the photocatalytic reaction. As the light energy source, it is possible to use a natural light source from the sun, as well as an artificial light source such as light from a mercury lamp, light from a fluorescent lamp, light from a filament lamp like a halogen lamp, light from a short-arc xenon lamp, and a laser beam. In addition, as an auxiliary light source for the rays of the sun, an artificial light source may be concurrently used.

As the method of irradiation, it is possible to use a method in which the light is directly radiated onto the metal-oxide film formed on the material, or, in the case of a luminous material, it is possible to use a method in which the light is radiated from the material after the light source is removed to activate the photocatalyst, or used jointly with a light source to irradiate the film.

In the present invention, if light is radiated onto the material on which a metal-oxide film exhibiting photocatalytic activity is formed, odors, molds, and the like (hereafter referred to as unwanted substances), which adhere to or are in contact with the surface of the material where the film is formed, can be decomposed and removed photochemically through the photocatalytic activity of the film. Accordingly, unlike conventional techniques, physical labor, large-scale equipment and facilities, and maintenance are practically unrequired. Unwanted substances can be decomposed and removed economically and simply. Compared with conventional catalysts, such as oxidation catalysts, the metal oxides used as the photocatalyst in the present invention undergo a small decline in activity due to heat deterioration and poisoning elements, so that the functions of decomposing and removing the unwanted substances, i.e., the deodorizing property, the antimold property, and the like are maintained over long periods of time. In addition, the material with the film formed thereon in accordance with the present invention absorbs ultraviolet rays. The mechanism of decomposing and removing unwanted substances on the metal-oxide film, which shows the photocatalytic activity is as follows, as the light energy is made incident upon the metal-oxide film by irradiation, active electrons and holes are produced on the surface of the metal oxide. These electrons and holes react directly with the unwanted substances, or active OH radicals, which are produced by the unwanted substances. This is thought to be the mechanism of reforming the unwanted substances.

The present invention is a deodorizing material comprising a light absorbing substrate and a film formed on said substrate, said film capable of decomposing mold, bacteria and odorous compounds, wherein an outer surface region of said film for receiving light is substantially formed of a metallic oxide which exhibits photocatalytic activity upon irradiation by ultraviolet light.

Advantageously, light absorbing substrate stores the absorbed light. Preferably, the light absorbing substrate emits at least a portion of the absorbed light upon a decrease in or elimination of the source providing the light. Advantageously, the substrate is selected from the group consisting of metals, plastics, composites, and paper. Preferably, the substrate exhibits phosphorescence upon a decrease in or elimination of the source providing the light.

Advantageously, the metallic oxide film is titanium dioxide. More advantageously, the film is anatase titanium dioxide. Advantageously, the substrate is coated with a luminous material. Preferably the luminous material is paint or a luminous sheet. Most preferably, the phosphorescence of the substrate provides light which activates or increases the photocatalytic activity of the film.

The photocatalyzing characteristics of the present invention are produced by titanium dioxide which transforms the metal oxide layer into a hydroxide ion. The hydroxide ion is effective against germs, bacteria, mold, and the like because of its strong oxidation potential. The hydroxide ion has more powerful oxidation characteristics than chloride ($Cl_2$) or ozone ($O_3$), which are commonly used in sterilizing processes, therefore it can also be useful to decompose oil or proteins. When the hydroxide ion contacts bacterial it damages the cell walls and kills the bacteria in a short period of time.

EXAMPLE 1

Formation of Titanium Dioxide on a Plastic Plate by Coating

Transparent plastic plates of 10 cm×20 cm were prepared.

A 2.5 mg/mL titanium dioxide solution was prepared by mixing 50 mg of anatase titanium dioxide powder with 10 ML of deionized water. After mixing, 0.5 ML of $RuCl_3$ was dissolved into the solution. The solution was then stirred for 1 minute.

The base material was thoroughly cleaned with a cotton plug immersed in a 95% ethanol.

After the base material was completely dried, the front surface of the base material was lacquer sprayed for 10 seconds and then, within 30 seconds, 10 mL of the titanium dioxide solution containing $RuCl_3$ was sprayed on to the lacquer-coated surface of the material.

The surface of the material was then completely dried (in approximately 30 minutes.)

EXAMPLE 2

Formation of the Luminous Material on to the Prepared Titanium Dioxide Plate 10 mL of luminous paint was sprayed onto a plate prepared in Example 1, on the surface that was not coated with $TiO_2$. The plate was then air-dried for 30 minutes.

EXAMPLE 3

A 10 cm×20 cm luminous sheet was taped, using double sided tape, to the uncoated side of a plate prepared in Example 1.

EXAMPLE 4

Preparation of Starting Materials

Polypropylene plates—(10 cm×20 cm×1 mm (+/−0.5 mm) (thickness)

Titanium dioxide (anatase type)—50 mg

Nitrocellulose—200 mg (to prevent exploding nitrocellulose, isopropyl alcohol was sprayed onto the powder prior to usage)

$RuCl_3$—5 mg

Methyl Ethyl Ketone (2-butanone)

Formation of Titanium Dioxide on Plastic by Coating 1. 100 mg of nitrocellulose was dissolved in a 10 mL of methyl ethyl ketone and immediately a polypropylene plate was sprayed with or dipped into the methyl ethyl ketone solution.
2. The mesh so formed was then dried for 5 minutes.
3. In a separate container, 100 mg of nitrocellulose, 50 mg of titanium dioxide and 5 mg of $RuCl_3$ were completely dissolved and mixed in 15 cc of methyl ethyl ketone.
4. One side of the dried plate was then sprayed with or dipped into the solution from #3 above.

The methyl ethyl ketone evaporated almost immediately and did not remain on the surface. Thus the problem of having organic compounds on the surface was avoided. Titanium dioxide will decompose organic compounds on the surface.

EXAMPLE 5

10 mL of luminous paint was sprayed onto the uncoated side of a plate prepared in Example 4. The plate was then air-dried for 30 minutes.

EXAMPLE 6

A 10 cm×20 cm luminous sheet was taped, using double sided tape, to the uncoated side of a plate prepared in Example 4.

EXAMPLE 7

The plate prepared in Example 6 was placed in a closed plastic container and the container exposed to UV light (200–400 nm) while the experiment was conducted. A kisenon lamp was used as a light source.

0.5 mL of $NH_3$ was placed in the closed plastic container. The results were as follows:

50% of the $NH_3$ was reduced after 60 min.
80% of the $NH_3$ was reduced after 90 min.
98% of the $NH_3$ was reduced after 120 min.

EXAMPLE 8

Two of the plates that were coated with the $TiO_2$ solution in Example 5 were placed in a closed container and exposed to light and $NH_3$ according to the procedure of Example 7. The results were as follows:

80% of the $NH_3$ was reduced after 60 min.
98% of the $NH_3$ was reduced after 90 min.

EXAMPLE 9

Three of the plates that were coated with the $TiO_2$ solution in Example 6 were placed in a closed container and exposed to light at $NH_3$ according to the procedure in Example 7. The results were as follows:

80% of the $NH_3$ was reduced after 10 min.
98% of the $NH_3$ was reduced after 30 min.

EXAMPLE 10

1. A 40L size transparent closed container was prepared as shown in FIG. 1.

2. A small fan was placed in the closed container for better circulation.
3. 4–10 cm 20 cm $TiO_2$ plates prepared in accordance with Example 2 were placed in the container.
4. Ammonia was placed in the container.
5. Until the concentration of ammonia reaches 500 ppm, a small hole in the container was opened.
6. Every 1 hr, UV light (390 nm) was exposed to the transparent closed container for 1 minute.
7. The concentration of ammonia was measured with a gas detector made by Gastec.

| Time (min) | NH3 Concentration (PPM) UV exposed every 10 min | NH3 Concentration (PPM) UV exposed all the time |
| --- | --- | --- |
| 0 | 500 | 500 |
| 30 | 450 | 400 |
| 60 | 400 | 320 |
| 120 | 300 | 200 |
| 200 | 250 | 140 |
| 260 | 200 | 100 |
| 320 | 170 | 70 |
| 500 | 110 | 40 |
| 620 | 100 | 20 |

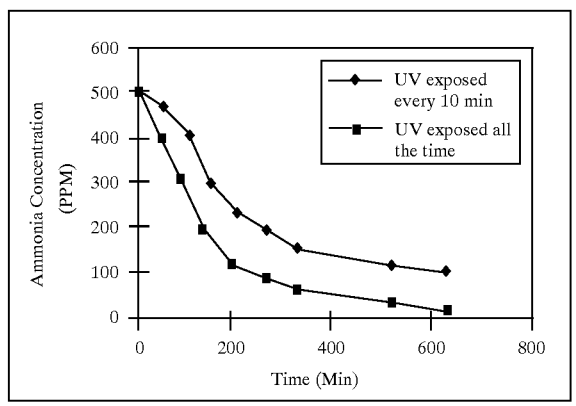

EXAMPLE 11

1. The steps 1 through 7 were repeated as described in Example 10 except that the initial concentration of ammonia was 310 ppm.

| Time (min) | NH3 Concentration (PPM) UV exposed every 10 min | NH3 Concentration (PPM) UV exposed all the time |
| --- | --- | --- |
| 0 | 310 | 310 |
| 60 | 230 | 160 |
| 120 | 140 | 100 |
| 180 | 110 | 70 |
| 240 | 95 | 50 |

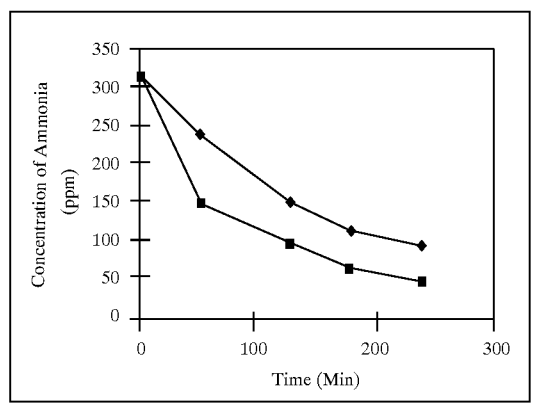

EXAMPLE 12

The steps 1 through 7 were repeated as described in Example 10 except that the initial concentration of ammonia was 75 ppm.

| Time (min) | NH3 Concentration (PPM) UV exposed every 10 min | NH3 Concentration (PPM) UV exposed all the time |
| --- | --- | --- |
| 0 | 75 | 75 |
| 60 | 50 | 42 |
| 120 | 35 | 25 |
| 180 | 30 | 20 |
| 240 | 25 | 17 |

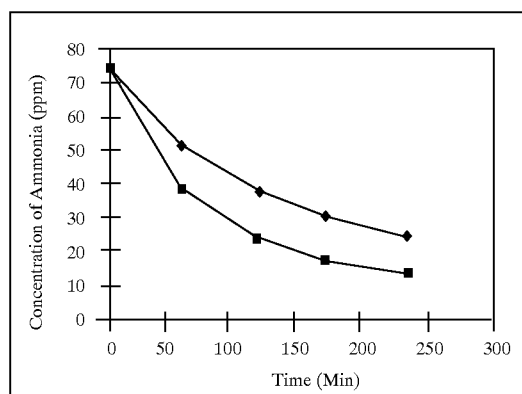

What is claimed is:
1. A deodorizing material comprising:
   a. a substrate coated with a luminous, light absorbing material; and
   b. a film formed on said substrate, said film capable of decomposing mold, bacteria and odorous compounds, wherein an outer surface region of said film for receiving light is substantially formed of a metallic compound which exhibits photocatalytic activity upon irradiation by ultraviolet light selected from the group consisting of $TiO_2$, ZnO, $SrTiO_3$, CdS, CdO, CaP, InP, $In_2O_3$, CaAs, $BaTiO_3$, $K_2NbO_3$, $Fe_2O_3$, $Ta_2O_5$, $WO_3$, $SaO_2$, $Bi_2O_3$, NiO, $Cu_2O$, SiC, $SiO_2$, $MoS_2$, $MoS_3$, InPb, $RuO_2$, and $CeO_2$.
2. The deodorizing material of claim 1 wherein the light absorbing material on the substrate stores the absorbed light.

3. The deodorizing material of claim 2 wherein the light absorbing material on the substrate exhibits phosphorescence upon a decrease in or elimination of the source providing the light.

4. The deodorizing material of claim 3 wherein the phosphorescence of the light absorbing material on the substrate provides light which activates or increases the photocatalytic activity of the film.

5. The deodorizing material of claim 1 wherein the light absorbing material on the substrate emits at least a portion of the absorbed light upon a decrease in or elimination of the source providing the light.

6. The deodorizing material of claim 1 wherein the substrate is selected from the group consisting of metals, plastics, composites and paper.

7. The deodorizing material of claim 1 wherein the metallic compound film is titanium dioxide.

8. The deodorizing material of claim 7 wherein the metallic compound film is anatase titanium dioxide.

9. The deodorizing material of claim 1 wherein the luminous material is a paint.

10. The deodorizing material of claim 1 wherein the luminous material is a sheet.

* * * * *